United States Patent [19]

Buechler et al.

[11] Patent Number: 5,237,057
[45] Date of Patent: Aug. 17, 1993

[54] TETRAHYDROCANNABINOL DERIVATIVES AND PROTEIN AND POLYPEPTIDE TETRAHYDROCANNABINOL DERIVATIVE CONJUGATES AND LABELS

[75] Inventors: Kenneth F. Buechler, San Diego; Si S. Moi, Escondido, both of Calif.

[73] Assignee: Biosite Diagnostics, Inc., San Diego, Calif.

[21] Appl. No.: 864,106

[22] Filed: Apr. 6, 1992

[51] Int. Cl.$^5$ .................... C07H 13/02; C07D 409/06

[52] U.S. Cl. ...................................... 536/119; 549/60; 549/390; 536/115

[58] Field of Search .................... 549/60, 390; 536/25, 536/115, 119

[56] References Cited

U.S. PATENT DOCUMENTS

| | | | |
|---|---|---|---|
| 4,690,944 | 9/1982 | Chiesi et al. | 549/60 |
| 4,833,073 | 5/1989 | McNally et al. | 435/7 |
| 5,144,030 | 9/1992 | Wang et al. | 549/390 |

FOREIGN PATENT DOCUMENTS

| | | | |
|---|---|---|---|
| 0279308 | 8/1988 | European Pat. Off. | |
| 2091721 | 8/1982 | United Kingdom | 549/390 |

OTHER PUBLICATIONS

Law, B., et al., Forensic Aspects of the Metabolism and Excretion of Cannabinol Following Oral Ingestion of Cannabis Resin, J. Pharm. Pharmacol. 36:289–294 (1984).

Schwartz, Alan and Madan, Pradeep, A Convenient Synthesis of 11-Nor-$\Delta$8-tetrahydrocannabinol-9-carboxylic Acid, J. Org. Chem. 51:5463–5465 (1986).

Wall, Monroe E. and Perez-Reyes, Mario, The Metabolism of $\Delta^9$-tetrahydrocannabinol and Related Cannabinoids in Man, J. Clin. Pharmacol., 21:1785–1895 (1981).

Williams, P. L. and Moffat, A. C., Identification in Human Urine of $\Delta^9$-tetrahydrocannabinol-11-OIC Acid Glucuronide: A Tetrahydrocannabinol Metabolite, J. Pharm. Pharmacol. 32:445–448 (1980).

Fahrenholtz, K. E., et al., The Total Synthesis of dl-$\Delta$-9-Tetrahydrocannabinol and Four of its Isomers, J. Am. Chem. Socy. 89:5934–5941 (1967).

Nordqvist, M., et al., Identification of a Major Metabolite of Tetrahydrocannabinol in Plasma and Urine from Cannabis Smokers, in Mass Spectrometry on Drug Metabolism (E. Ghisalberai, ed.) Plenum Press, N.Y. (1977).

Pitt, Colin G., et al., The Preparation of 5′-Iodo-$^{125}$I--$\Delta^8$-THC; A Radioligand for the Radioimmunoassay of Cannabinoids, J. Labelled Comp. and Radiopharmaceuticals, 17:681–689 (1978).

Pitt, C. G., et al., The Synthesis of Deuterium, Carbon-14, and Cancer Free Tritium Labeled Cannabinoids, J. Labelled Comp. 11:551–575 (1978).

Rodgers, Richard et al., Homogeneous Enzyme Immunoassay for Cannabinoids in Urine, Clin. Chem. 24:95–100 (1978).

Mago, E., et al., An Alternative Route for the Synthesis of Unlabelled and Labelled Delta-1-tetrahydrocannabinol-7-OIC acid, reprinted in Marihuana '84 Proceedings of the Oxford Symposium on Cannabis (D. J. Harvey, ed.) IRL Press, Ltd., Oxford, England (1984).

Seltzmann, H. H., et al., Syntheses of Cannabinoid Radioligands and Haptens for Use in Radioimmunoassay and Receptor Site Studies, Reprinted in Marihuana '84 Proceedings of the Oxford Symposium on Cannabis (D. J. Harvey, ed.) IRL Press, Ltd., Oxford, England (1984).

Al-Hakawati, M. I. and Paris, M., Advanced High Pressure Liquid Chromatography (HPLC) Method for the Analysis of Cannabinoids in *Cannabis sativa* L., reprinted in Marihuana '84 Proceedings of the Oxford Symposium on Cannabis (D. J. Harvey, ed.) IRL Press, Ltd., Oxford England (1984).

*Primary Examiner*—Mark Russell
*Attorney, Agent, or Firm*—Lyon & Lyon

[57] ABSTRACT

The present invention is directed to novel THC derivatives which are synthesized for the covalent attachment to antigens (proteins or polypeptides) for the preparation of antibodies or receptors to the THC metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

4 Claims, 1 Drawing Sheet

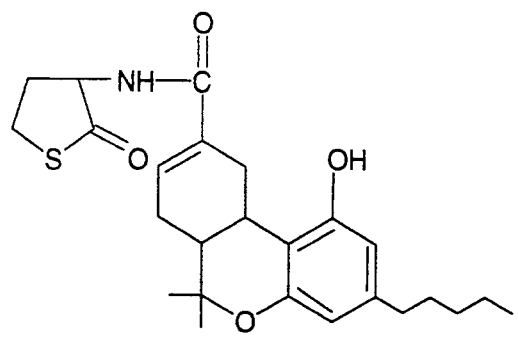
EXAMPLE 1
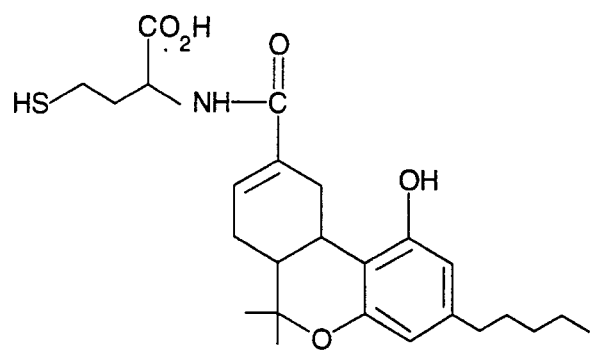
EXAMPLE 2
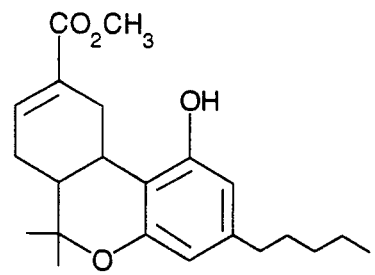
EXAMPLE 3
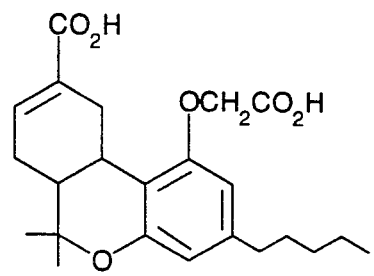
EXAMPLE 4
FIG_1

TETRAHYDROCANNABINOL DERIVATIVES AND PROTEIN AND POLYPEPTIDE TETRAHYDROCANNABINOL DERIVATIVE CONJUGATES AND LABELS

FIELD OF THE INVENTION

This invention is in the field of ligand receptor assays, including immunoassays, for the detection of selected metabolites of tetrahydrocannabinol in a fluid sample. More particularly, this invention relates to methods for the synthesis of novel tetrahydrocannabinol derivatives and protein and polypeptide tetrahydrocannabinol derivative conjugates and labels for use in the preparation of antibodies to tetrahydrocannabinol metabolites and for use in the immunoassay process.

BACKGROUND OF THE INVENTION

1-$\Delta^9$-Tetrahydrocannabinol (THC) is the most psychoactive constituent of the marihuana plant (*Cannabis sativa*). The use of marihuana can result in euphoria, hallucinations, sedation and temporal distortion. Its widespread abuse has prompted a need to monitor the use. THC is metabolized to a variety of psychoactive and inactive derivatives and the majority of the metabolites are excreted in the urine as glucuronides (Life Sci. 17, 1637 (1975), Res. Comm. Chem. Path. Pharm. 17, 421 (1977) and Clin. Pharm. Ther. 34, 352 (1983)).

The preparation of antibodies to THC metabolites requires the synthesis of a THC derivative in order to covalently attach the derivative to an antigenic polypeptide or protein. In addition, the THC derivative is covalently attached to various polypeptides, proteins or labels for use in screening antibodies and in the immunoassay process. The THC derivative should mimic the structure of the THC metabolite sought to be measured. Therefore, the selection and synthesis of the types of THC derivatives for covalent attachment to proteins, polypeptides or labels is critical. In addition, the THC derivatives need to be stable and soluble in an aqueous solution.

THC compounds and conjugates for immunization and immunoassay have been described in U.S. Pat. Nos. 4,833,073 and Euro. Pat. Appl. No. 279,308.

SUMMARY OF THE INVENTION

The present invention is directed to novel THC derivatives which are synthesized for the covalent attachment to antigens (proteins or polypeptides) for the preparation of antibodies to the THC metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids and tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the composition between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1-20 carbons and 0-10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon—carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted "Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1-or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO— or HCO—.

The terms "acylamino" refers to RCONCR)— and (RCO$_2$N— respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonymethyl" refers to hydrocarbyl—OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon—carbon double bond and includes straight-chain, branched-chain and cyclic groups.

The term "alkynyl" refers to unsaturated hydrocarbyl groups which contain at least one carbon—carbon triple bond and includes straight-chain, branched-chain and cyclic groups.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methene" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

"Thioether" refers to C—S—C.

"Ester" refers to

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or noncompetitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DESCRIPTION OF THE DRAWING

FIG. 1 depicts the structures of the compounds of Examples 1-4.

DETAILED DESCRIPTION OF THE PREFERRED EMBODIMENTS

Novel compounds are described which are used in the generation of antibodies and in the immunoassay process generally. The compounds are derivatives of THC metabolites. The derivatization of the THC analogue for covalent attachment to proteins, polypeptides and labels occurs on the 9-carboxy or 1-hydroxy position of 1-$\Delta^8$-9-carboxytetrahydroxycannabinol (cTHC). The synthesis of the linking group chemical arm between the protein, polypeptide or label and the cTHC derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

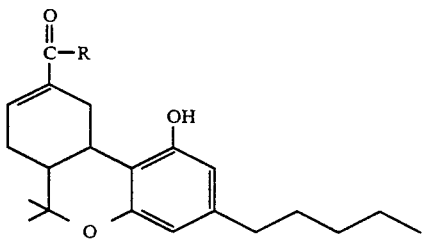

where R is a linking group comprising one of the following;

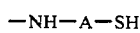

—NH—A—SH

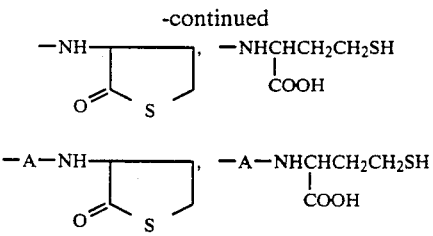

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula:

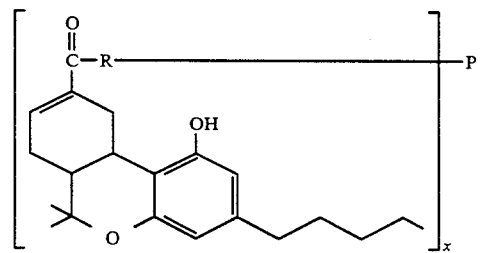

where P is an antigenic protein or polypeptide or a protein, polypeptide or label;
where x is at least one and not greater than 100;
where R is a linking group of the following:

—NH—A—S—B—

—NHCHCH$_2$CH$_2$S—B—
|
COOH

—A—NHCHCH$_2$CH$_2$S—B—
|
COOH where A is a linking group of from 1 to 20 carbons and 0 to 10 heteroatoms (NH, O, S), either branched or straight chain;

where B is a linking group ultimately attached to a protein, polypeptide or label selected from the group comprising:

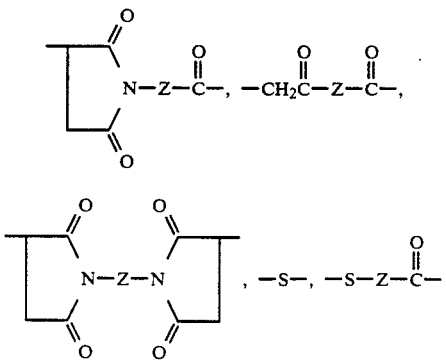

where Z is a linking group of from 1 to 20 carbons and 0 to 10 heteroatoms (NH, O, S) and may be branched or straight chain.

In general, the compounds of this invention also have the following formula:

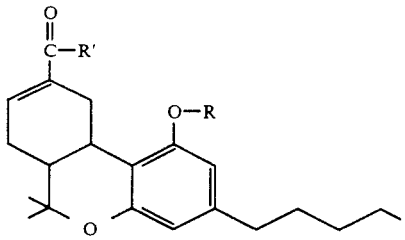

where R' is —OH or a glucuronide ester;
where R is a linking group comprising one of the following:

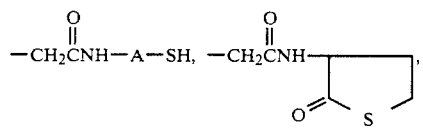

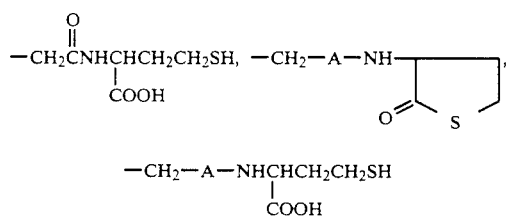

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label also to a compound of the formula is of the following:

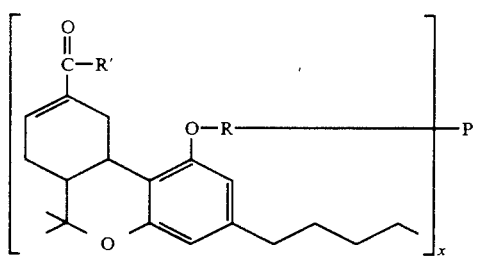

where P is an antigenic protein or polypeptide or a protein, polypeptide or label;
where x is at least one and not greater than 100;
where R' is —OH or a glucuronide ester
where R is a linking group of the following:

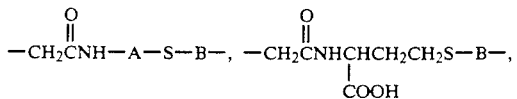

-continued

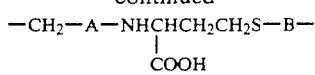

where A is a linking group of from 1 to 20 carbons and 0 to 10 heteroatoms (NH, O, S) either branched or straight chain;
where B is a linking group ultimately attached to a protein, polypeptide or label selected from the group comprising:

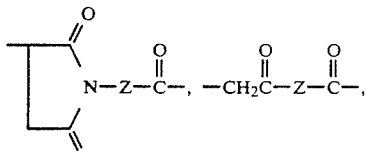

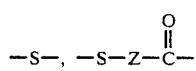

where Z is a linking group of from 1 to 20 carbons and 0 to 10 heteroatoms (NH, O, S) and may be branched or straight chain.

The preferred (best mode) compounds of this invention have the following formula:

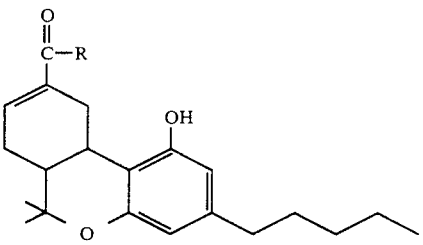

where R is a linking group comprising one of the following:

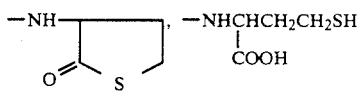

In addition, the general form of the preferred (best mode) immunogenic protein or polypeptide molecule or the protein or polypeptide molecule or label derivatized via an amide or ester bond to the molecule or label to a compound of the formula is of the following:

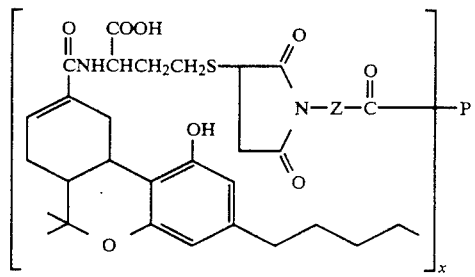

where P is an antigenic protein or polypeptide or a protein, polypeptide or label;
where x is at least one and not greater than 100;

where Z is a linking group of from 1 to 20 carbons and 0 to 10 heteroatoms (NH, O, S) and may be branched or straight chain.

The preferred (best mode) compounds of this invention also have the following formula:

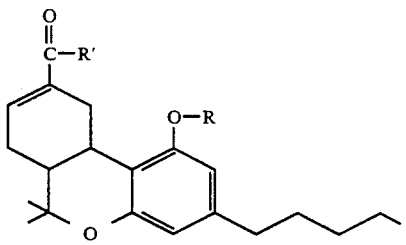

where R' is —OH or a glucuronide ester where R is a linking group comprising one of the following;

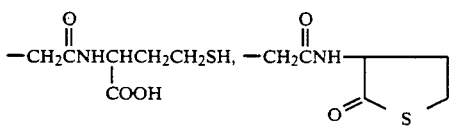

Also, in addition, the general form of the preferred (best mode) immunogenic protein or polypeptide molecule or the protein or polypeptide molecule or label derivatized via an amide or ester bond to the molecule or label to a compound of the formula is of the following:

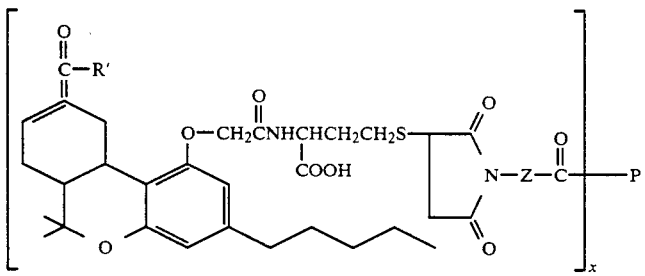

where P is an antigenic protein or polypeptide or a protein, polypeptide or label;

where x is at least one and not greater than 100;

where R' is —OH or a glucuronide ester where Z is a linking group of from 1 to 20 carbons and 0 to 10 heteroatoms (NH, O, S) and may be branched or straight chain.

Of particular interest are cTHC derivatives which have been synthesized using the l-stereoisomer since this isomer exists in nature. The cTHC derivatives of the present invention are synthesized as the l-isomers to raise highly specific and high affinity antibodies to cTHC. The hydrophobic nature of the cTHC molecule causes it to adsorb to plastic and glass surfaces and to proteins. Thus, the cTHC derivatives of the present invention are synthesized such that a carboxylic acid group is introduced into the molecule to improve the water solubility of the derivative. This is particularly important because when immunogens and protein conjugates are prepared a number of THC derivatives, roughly 1–100, are covalently attached to the protein, polypeptide or label. The high degree of substitution can cause the precipitation of the protein or polypeptide conjugate or label if additional water solubilizing groups, for example, carboxylic acids and sulfonic acids, are not incorporated onto the cTHC derivative. In addition, in the absence of water solubilizing groups on the THC derivative which is covalently attached to the protein or polypeptide, the THC derivative can more readily adsorb to the protein surface or can interact with each other at the protein surface resulting in fewer THC derivatives available to bind the receptor. Thus, when the covalently attached THC derivatives interact with each other or are adsorbed to the protein or polypeptide surface the binding affinity of the receptor for the THC conjugate is decreased. In general, for immunoassays, the highest possible binding affinity is preferred because this allows for a sensitive and rapid immunoassay (for example, see U.S. Pat. Nos. 5,028,535 and 5,089,391). The novel THC derivatives described herein provide improved water solubility.

The alkylation of the 1-OH of the 9-glucuronide ester of cTHC with an alkyl halide thiol ester, such as 2-(2-amino-4-thiolbutanoic acid thiolactone)-bromoacetamide, is accomplished under conditions used to synthesize the 1-0-alkylated cTHC derivative as described herein. The esterification of the 1-OH of the 9-glucuronide ester of cTHC with a carboxylic acid alkyl thiol ester, such as acetylthiopropionic acid, is accomplished under usual conditions for forming aromatic esters.

The 1-$\Delta^8$-9-carboxytetrahydrocannabinol was used for the synthesis of the THC derivatives rather than the $\Delta^9$ isomer because the former is more stable to isomerization. One skilled in the art can recognize that the teachings described herein can be applied to the $\Delta^9$ isomer.

The THC derivatives are also synthesized as thiols or thiol esters so that their covalent attachment to proteins, polypeptides or labels can easily be performed under mild conditions, for example, pH 7 in a protein solution. The linking arm between the drug derivative and the thiol or thiol ester can be of various lengths. For example, the 9-carboxyTHC can be directly reacted with homocysteine thiolactone or the 9-carboxyTHC can first be reacted with varying chain lengths of an aminoalkyl carboxylic acid ester, for example, 4-aminobutyric acid methyl ester, the ester then hydrolyzed in mild base and the resulting carboxylic acid THC derivative can then be reacted with homocysteine thiolactone. The thiol esters are simply hydrolyzed in dilute base, for example, 0.01 M–0.1 M potassium hydroxide, to generate the thiol group which is reacted with the thiol reactive group, such as a maleimide, an alkyl halide or a thiol. The thiol reactive group is generally on the protein, polypeptide or label but can also be incorporated onto the protein, polypeptide or label after the thiol drug reacts with the thiol reactive compound.

The protein, polypeptide or label is reacted with a reagent which incorporates a maleimide or alkylhalide into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol, but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the THC thiol derivatives. Conversely, the bis-maleimide compound can be reacted with the thiol derivative and subsequently to the thiol containing protein, polypeptide or label. Common bis-maleimides are bis-maleimidohexane from Pierce, N,N'-bis(3-maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wis. The thiol THC derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 5,028,535 and 5,089,391.

EXPERIMENTAL EXAMPLES Example 1 Synthesis of 9-N-(2-Butyrothiolactone)amido-11-nor-$\Delta^8$-Tetrahydrocannabinol Using 1-9-Carboxy-$\Delta^8$-11-nor-tetrahydrocannabinol (400 mg, $1.2 \times 10^{-4}$ mol, Research Triangle Institute, Research Triangle Park, N.C.) was dissolved in anhydrous pyridine (12 ml). dl-Homocysteine thiolactone hydrochloride (196 mg, $1.3 \times 10^{-3}$ mol) was added to the solution followed by 1-(3-dimethylaminopropyl)-3-ethylcarbodiimide hydrochloride (0.44 g, $2.3 \times 10^{-3}$ mol. The flask was purged with argon and the reaction mixture stirred at 25° C. for 6 h. The solvent was removed in vacuo, and ethanol was added ($3 \times 25$ ml) to azeotrope any residual pyridine. The residue was partitioned between 0.5 M potassium phosphate, pH 7.0 (25 ml) and chloroform (25 ml). The chloroform layer was washed with deionized water ($3 \times 30$ ml), and dried over anhydrous magnesium sulfate. The drying agent was removed by filtration. The solvent was removed in vacuo to give 480 mg of the final product.

Example 2 Synthesis of 9-N-(Cysteine)amido-11-nor-$\Delta^8$-Tetrahydrocannabinol 9-N-(2-Butyrothiolactone)amido-11-nor-$\Delta^8$-Tetrahydrocannabinol (0.89 mg, $2 \times 10^{-6}$ mol) was dissolved in 0.07 ml dimethylformamide/water (70/30, v/v). Potassium hydroxide (0.02 ml, 1 N) was added and the solution sat at room temperature for 10 min. Potassium phosphate buffer (0.1 ml, 0.5 M, pH 7), was immediately added. The title compound in solution was used as is to react with thiol reactive groups, such as maleimides, alkyl halides or thiols, which are either free in solution or are coupled to proteins, polypeptides or labels.

Example 3 Synthesis of 9-Carboxy-11-nor-$\Delta^8$-tetrahydrocannabinol Methyl Ester A solution of 9-carboxy-11-nor-$\Delta^8$-tetrahydrocannabinol (10 mg, $2.9 \times 10^{315}$ mol) in methyl alcohol (1 ml) containing 1 M hydrogen chloride in diethyl ether (0.1 ml) was heated at 55° C. for 2 h. The solvent was evaporated under vacuum to afford 10.4 mg (100%) of the title compound as a clear gum.

Example 4 Synthesis of 9-Carboxy-11-nor-$\Delta^8$-1-O-Carboxymethyltetrahydrocannabinol To a solution of 9-carboxy-11-nor-$\Delta^8$-tetrahydrocannabinol methyl ester (1.0 mg, $2.8 \times 10^{-6}$ mol) in anhydrous dimethylformamide (80 μl) containing sodium hydride (0.1 mg, $4.2 \times 10^{-6}$ mol) was added ethyl bromoacetate (0.5 mg, $2.7 \times 10^{-6}$ mol). The reaction mixture was heated at 50° C. for 5.5 h. Additional sodium hydride (0.06 mg, $2.5 \times 10^{-6}$ mol) in anhydrous dimethylformamide (60 μl) was added to the solution and heated at 50° C. for a total of 6 h. The solvent was removed in vacuo. The residue was dissolved in methyl alcohol (250 μl), followed by water (200 μl), and 1 N potassium hydroxide (50 μl) was added. The reaction was heated at 75° C. for 45 min. Hydrogen chloride (1 N) solution was added to adjust pH to 7.0, and the solvent removed in vacuo. The residue was dissolved in water, and acidified to pH 2.0 with hydrogen chloride (1 N) solution. The solution was extracted with chloroform (1 ml $\times$ 1), and dried under argon to yield 3.9 mg of title compound as a clear residue.

We claim:

1. Compounds of the formula:

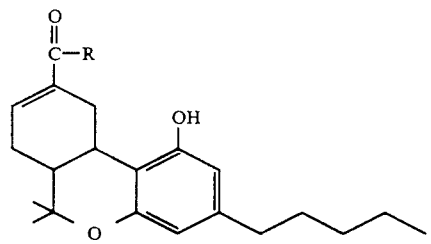

where R is a linking group consisting of one of the following:

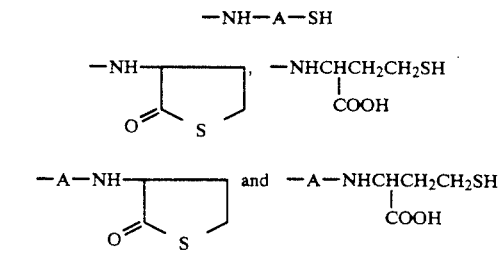

where A is a linking hydrocarbyl group of from 1 to 20 carbon atoms and 0 to 10 heteroatoms selected from the group consisting of nitrogen, oxygen, and sulfur, which may either be in the chain or substi- 2. Compounds of the formula:

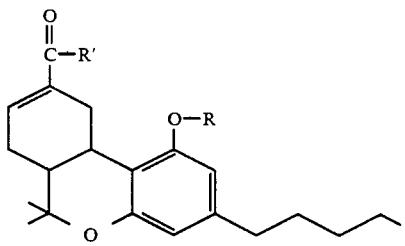

where R' is —OH or a glucuronide ester
where R is a linking group consisting of one of the following:

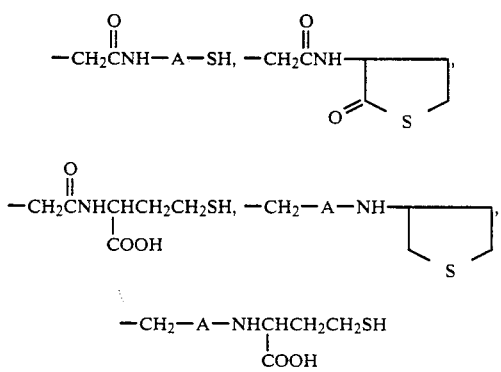

where A is a linking hydrocarbyl group of from 1 to 20 carbon atoms and 0 to 10 heteroatoms selected from the group consisting of nitrogen, oxygen, and sulfur, which may either be in the chain or substituted on the chain which may be straight or branched.

3. Compounds of the formula:

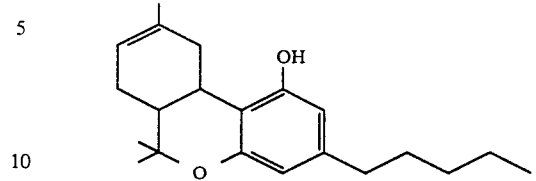

where R is a linking group consisting of one of the following:

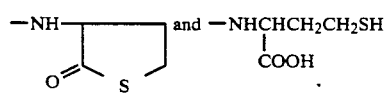

4. Compounds of the formula:

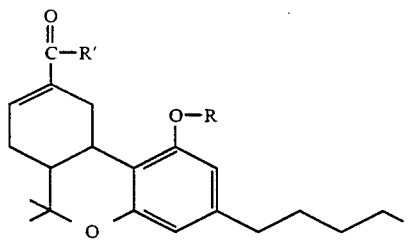

where R' is —OH or a glucuronide ester
where R is a linking group consisting of one of the following:

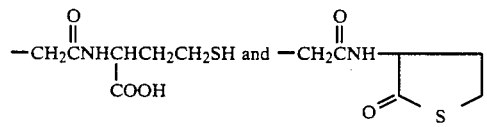

* * * * *

UNITED STATES PATENT AND TRADEMARK OFFICE
CERTIFICATE OF CORRECTION

PATENT NO. : 5,237,057
DATED : August 17, 1993
INVENTOR(S) : Kenneth F. Buechler and Si Shi Moi It is certified that error appears in the above-identified patent and that said Letters Patent is hereby corrected as shown below:

Column 3, line 13 should end with a period;

Column 11, line 46, delete "$10^{-3}$" and substitute --$10^{-4}$--;

Column 11, line 49, after "mol" insert --)--;

Column 12, line 9, delete "$10^{315}$" and substitute --$10^{-5}$--;

Column 3, line 66, delete "RCONCR)" and substitute --RCONCR--;

Column 3, line 67, delete "(RCO$_2$N" and substitute --RCO$_2$N--

In Claim 2, Column 13, lines 26 to 31, the formula should appear as follows:

Signed and Sealed this

Twenty-sixth Day of April, 1994

Attest:

BRUCE LEHMAN

Attesting Officer

Commissioner of Patents and Trademarks